United States Patent [19]

Li et al.

[11] Patent Number: 4,988,618
[45] Date of Patent: Jan. 29, 1991

[54] MAGNETIC SEPARATION DEVICE AND METHODS FOR USE IN HETEROGENEOUS ASSAYS

[75] Inventors: May K. Li, Framingham; Jack Kessler, Ashland; David T. Bach, Westborough, all of Mass.

[73] Assignee: GENE-TRAK Systems, Framingham, Mass.

[21] Appl. No.: 347,544

[22] Filed: May 3, 1989

Related U.S. Application Data

[63] Continuation of Ser. No. 121,191, Nov. 16, 1987, abandoned.

[51] Int. Cl.[5] .......................................... G01N 33/553
[52] U.S. Cl. .......................................... 435/6; 435/173;
435/301; 436/526; 436/808; 436/809; 422/104;
210/222; 210/695
[58] Field of Search .......................... 435/173, 301, 6;
210/222, 695; 209/9; 269/8; 422/104; 436/808,
809, 526

[56] References Cited

U.S. PATENT DOCUMENTS

| | | | |
|---|---|---|---|
| 3,402,820 | 9/1968 | Lohmann | 210/222 |
| 3,608,718 | 9/1971 | Aubrey, Jr. et al. | 210/222 X |
| 3,985,649 | 10/1976 | Eddelmann | 210/695 |
| 4,018,886 | 4/1977 | Giauer | 210/222 |
| 4,157,323 | 6/1979 | Yem et al. | 436/526 X |
| 4,272,510 | 6/1981 | Smith et al. | 436/526 X |
| 4,438,068 | 3/1984 | Forrest | 436/526 X |
| 4,710,472 | 12/1987 | Saur et al. | 435/287 |
| 4,711,271 | 12/1987 | Weisenbarger et al. | 210/222 X |

FOREIGN PATENT DOCUMENTS

| | | | |
|---|---|---|---|
| 0165219 | 12/1985 | European Pat. Off. | 435/301 |
| 2152664 | 8/1985 | United Kingdom | 436/526 |

OTHER PUBLICATIONS

"Magic", Corning Co. (Rochester) Brochure, Printed in U.S.A./Jun. 1983.

*Primary Examiner*—Carl D. Price
*Attorney, Agent, or Firm*—Mark A. Hofer; Anthony J. Janiuk

[57] ABSTRACT

Magnetic separation devices are described for use in immunoassay or hybridization assay procedures. The most preferred embodiments comprise a defined relationship between microtube and microtiter plate receiving orifices and rare earth cobalt magnets having predetermined magnetic field orientations.

17 Claims, 4 Drawing Sheets

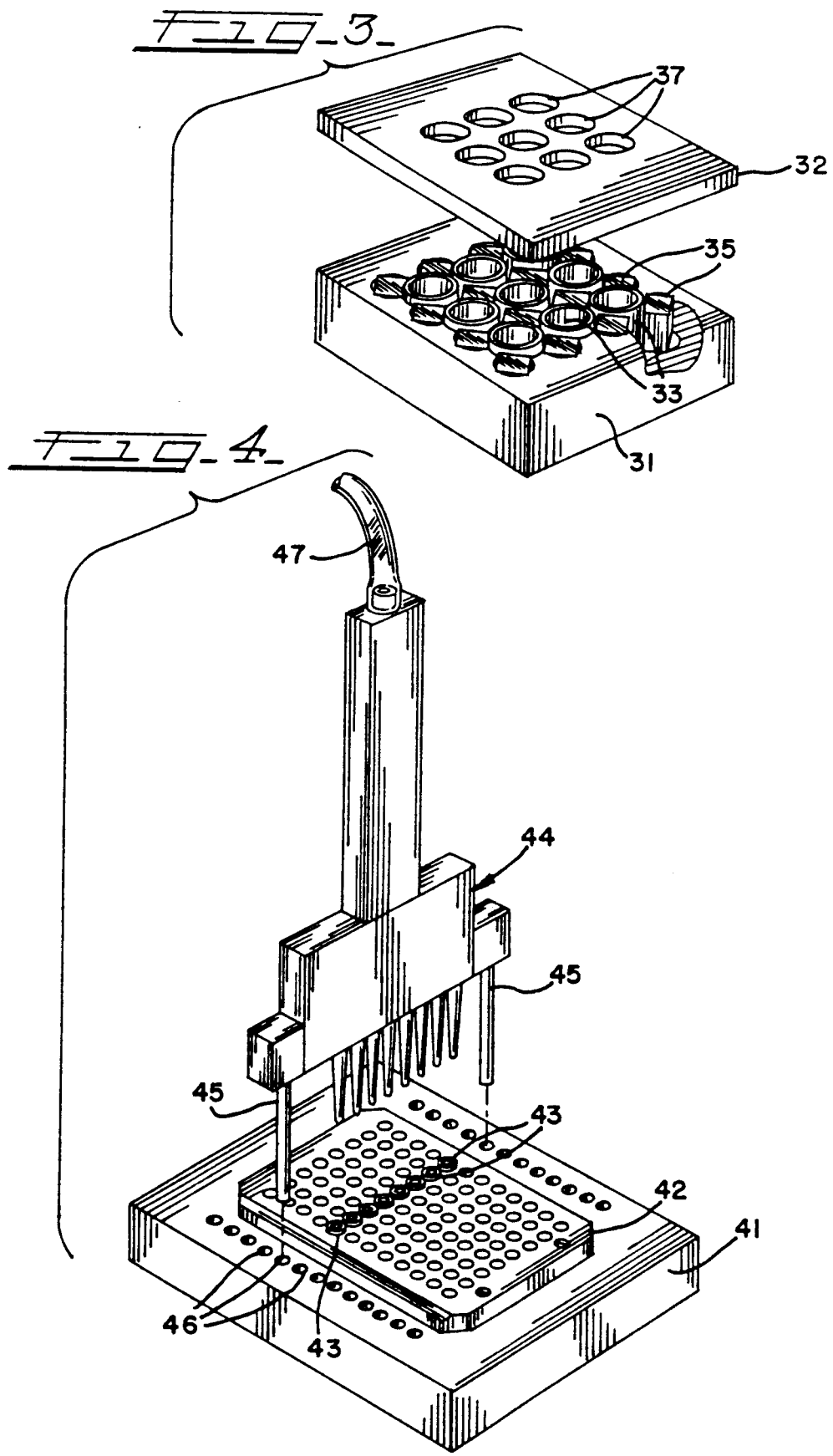

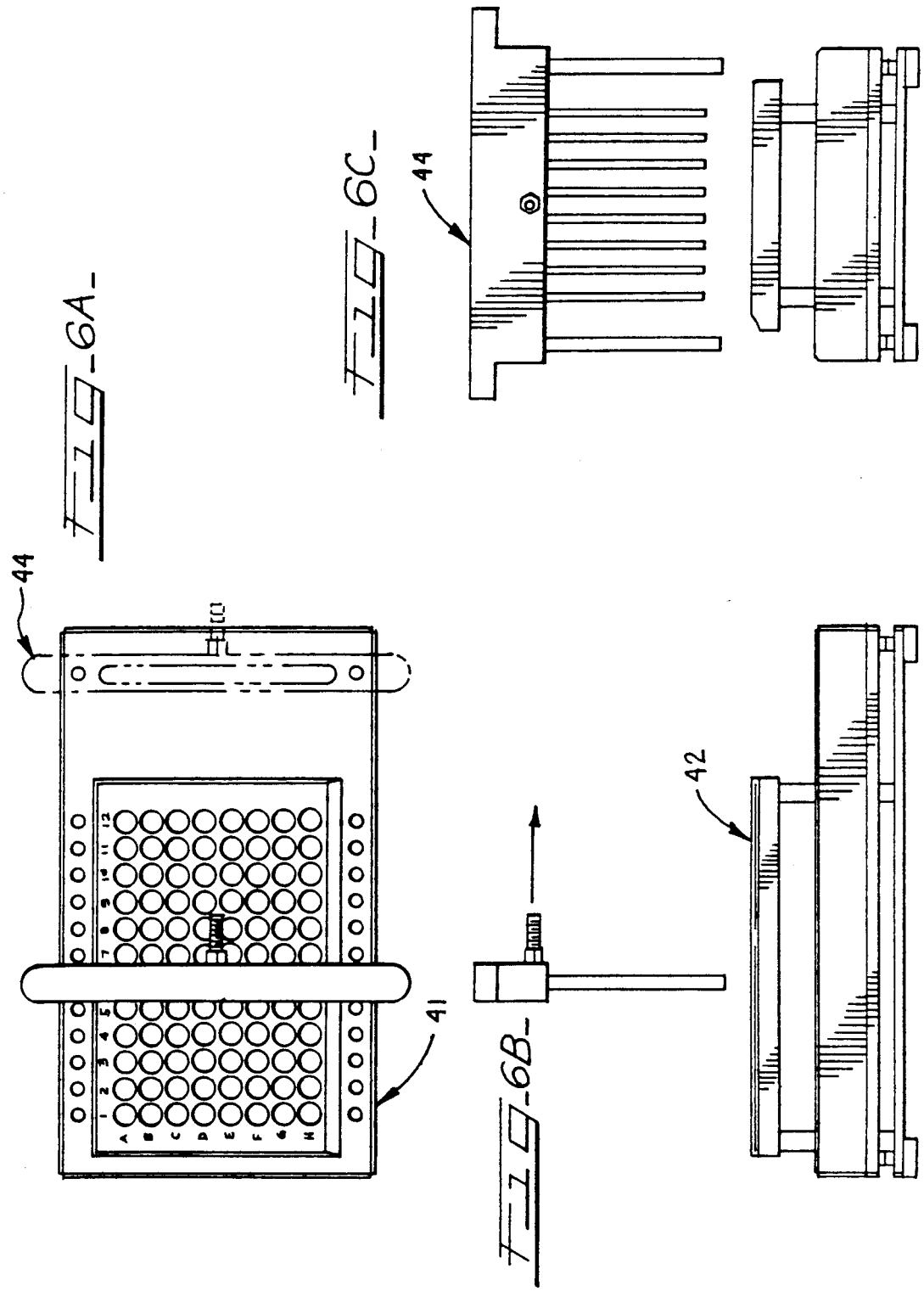

MAGNETIC SEPARATION DEVICE AND METHODS FOR USE IN HETEROGENEOUS ASSAYS

This is a continuation of co-pending application Ser. No. 121,191 filed on 11/16/87, now abandoned.

FIELD OF THE INVENTION

This invention relates to devices useful in performing heterogeneous type assays and more particularly describes new magnetic separation devices for use with immunoassay and hybridization type assays utilizing micromagnetic or ferrous particles.

BACKGROUND OF THE INVENTION

In recent years, health care has improved dramatically, in large measures due to the availability and improvement in assays. Assays detect particular chemical constituents, i.e., ligands, which have been correlated or are associated with various disease conditions. Ligands are detected primarily through a binding reaction with a ligand binding specific substance which preferentially binds to the ligand and not to other chemical constituents which may be present in the sample to be tested. Through a variety of imaginative techniques, the presence or absence of such a binding reaction can be detected, and thus in turn the presence or absence of the ligand in the sample determined.

There are two major types of assays to which this claimed invention relates and these include immunoassays and hybridization assays. Immunoassays have been in existence longer and are based upon the specificity of the reaction between an antibody and an antigen for which the antibody is specific. Antibodies initially used where of polyclonal origin, e.g., they were produced in animals following a challenge by the antigen for which the antibodies were desired. Of late, following the innovative developments by Koller and Millstein in 1975 (Nature 225:1061), monoclonal antibodies have been preferred since they can be more easily produced and allow exquisite selection by affinity and avidity.

There further exists a variety of techniques for labeling the antibodies and/or antigens including the employment of isotopic labels, fluorescent molecules, chemiluminescent molecules, enzymes, light scattering particles, energy transfer, schemes between pairs of spectrally matched molecules, and the like. These techniques are well known in the art and need not be reviewed in detail here. It is worthy, however, to distinguish between two diverse types of assays; homogenous and heterogeneous assays. Homogeneous are most desired from an operational standpoint since the entire reaction, and an addition of reagents for the performance of the assay, take place in a single solution along with the final detection step. Accordingly, mechanical manipulations which are time consuming and can cause errors are avoided, however, the technical aspects of developing such an assay with the desired sensitivity are substantial. In contrast, numerous assays are performed on a heterogeneous basis in that certain steps are performed in one solution which generally includes some type of solid phase material. The reaction to be detected takes place either in solution or on the solid phase and is then followed by a separation step whereby unreacted components, and thus contaminating influences, may be effectively removed. The result is generally a higher level sensitivity at the expense of additional mechanical manipulations. Conventional heterogeneous assays have employed dipsticks which may be easily removed from the solution by hand, or large beads which similarly allow facile transfer. Smaller beads, generally of latex or similar materials, have been employed and have relied upon filter and/or centrifugal methods for their sequestration from the fluids. The concept of employing large magnetic particles has also been explored and is described by Smith et al. in U.S. Pat. Nos. 4,272,510 and 4,292,920. Specifically, Smith et al. describe the use of BB type particles and their removal from solution by the employment of electromagnetic energized nails for removing the solid phase from container to container. While somewhat inelegant, the Smith et al. method does have an advantage in that the container walls which often provide a contaminating influence are eliminated assuming, of course, the detectable reaction has taken place on the solid phase. The methods, however, suffer from substantial risk of loss of accuracy due to the failure to remove and/or transfer all solid phase particles to another container, particularly as would be the case with micromagnetic or ferrous particles. Such microparticles would be greatly preferred over the large beads described by Smith et al. because the present has a far greater surface area upon which reactions may take place. Sensitivity is accordingly dramatically improved.

Corning et al. has made available commercially a magnetic separation device which is intended for use with large, e.g., 12 mm by 75 mm, test tubes containing the assay reagent mixtures and the magnetic particle solid phase component. The Corning device has horizontal molded ridges for receiving the test tube whereby the particles become attracted to a side of the test tube allowing removal of the liquids. The design of the Corning device is not, however, optimized for use with small sample volumes and cannot be made optimal for such application therefore limiting its utility.

It is an object of the present invention to provide devices for use with assays employing magnetic microparticles which are capable of use with small volume assays or >60 at a time.

It is another object of the present invention to provide devices which may be employed with microtiter type trays whereby a plurality of assays may be performed simultaneously.

It is yet another object of the present invention to provide an autoclavable separation devices for use with ferrous solid phase materials.

It is a still further object of the present invention to provide a magnetic separation device which is readily adaptable to automated pipetting systems.

It is still yet a further object of the present invention to provide a magnetic separation device which may be adapted to provide one, two or four ferrous particle attraction positions within each sample container.

Another class of assays of more recent vintage are those relying upon the hybridization of nucleic acid probes with target nucleic acids. The target nucleic acid is generally that associated with an infective organism, e.g., bacteria virus and like, although the detection of specific cellular genomes is also contemplated. By greatly simplified explanation, hybridization assays rely upon the greatly preferred pairings between complementary nucleotide bases. Specifically, the preferred pairings are between adenine and thymidine, guanine and cytidine. Each strand of deoxyribonucleic acid (DNA) is comprised of a series of the foregoing bases, while its complementary strand comprises a matching but complementary series of DNA bases. Thus, one can disassociate the double-stranded nucleic acid into single-strands and with probes comprised of nucleic acids having complementary sequences, one may produce double-stranded nucleic acid wherein the probe is hybridized to the target nucleic acid only at complementary positions.

DNA is transcribed into ribonucleic acid (RNA) which is also comprised of ribonucleotides of the same four bases with the exception that uracil is substituted for thymidine. Because of the manner of transcription, the RNA sequence is also complementary to the DNA sequence and accordingly comprises the same basic identifying information. Thus, one may similarly detect RNA of a microorganism or cell by hybridizing the target RNA to a probe comprising complementary sequence. The production and formulation of nucleic acid probes while a comparatively recent development, are still arts well known and well described in the literature. A helpful reference in this regard is Maniatis et al., a cloning manual, the relevant portions of which along with references referred to therein are incorporated herein by reference.

As may be readily appreciated, many of the same techniques employed with immunoassays are the labeling, and heterogeneous/homogenous schemes are applicable to hybridization assays. In particular, the employment of solid phase materials in heterogeneous assays are techniques which make hybridization assays especially useful. The utilization of micromagnetic particles is not, however, commonplace primarily in large measure due to the inapplicability of the present magnetic separation devices to hybridization assays.

It is, therefore, another object of the present invention to provide suitable magnetic separation devices useful with hybridization assays and ferrous solid phase particles.

SUMMARY OF THE INVENTION

In accordance with the principles and objects of the present invention, there are provided magnetic separation devices for use in heterogeneous immunoassay and/or hybridization assays which comprise a base having a plurality of orifices for receiving nonferrous containers which hold the sample and assay components including ferrous particles which may or may not exhibit a natural magnetism. Each of the orifices is surrounded by preferably, a plurality of magnetics, most preferably four, which are spaced, most preferably equidistant, about the peripheral of the orifice. The north-south field orientation of each magnet is preferably orientated so that it is coplanar with a cross-sectional plane through the receiving orifice and accordingly impinges upon the nonferrous container in a direction that is defectively perpendicular to the generally aligned axes of of the container. Ideally, the north-south field direction orientation of the magnetics about the periphery is in the same direction regardless of its position about the periphery of the orifice. Thus, all magnetics in this preferred embodiment are aligned in a single particular direction in relation to the base. More preferably, the north-south magnetic field orientation of the magnetics about the periphery of the receiving orifice are alternating 180° in direction. Thus, reviewing the field orientation of the magnetics by preceding in a common direction about the periphery of the orifice, e.g., clockwise or counterclockwise for each orifice, results in the first magnetic having a north-south field direction which is 180° opposing that of the next magnet which in turn is 180° opposing that of the following and so on. Thus, every other magnet about the periphery has a substantially identical field orientation.

Most preferred embodiments of the device further comprise a guided pipetting means capable of pipetting fluids to or from a plurality of the nonferrous containers simultaneously. Other embodiments further comprise means for agitating the reagents within each of the nonferrous containers and for incubating the nonferrous containers and a transfer slide adapted to engage the base means for mating the plurality of nonferrous containers to the receiving orifices and for removing same.

Other embodiments of the present invention comprise receiving orifice-magnet orientations which provide for one or two spot attraction sites within the nonferrous container while the most preferred embodiment above, having a receiving orifice surrounded by four magnets results in four spot attraction sites.

Novel processes are provided comprised of the magnetic separation devices of the present invention in immunoassay or hybridization assays for a ligand in a fluid sample.

BRIEF DESCRIPTION OF THE DRAWINGS

Further understanding of the invention including these and other principles and objects may be had upon study of the drawings wherein.

FIG. 3 shows a preferred embodiment of the magnetic separator device;

FIG. 4 shows a perspective view of the microtube tray mounted on the magnetic separator device with associated guided eight channel aspirator/pipetter;

FIGS. 6A, 6B and 6C shows several perspective views of a magnetic separator device with associated eight channel vacuum head for facile removal of waste fluid.

DETAILED DESCRIPTION AND BEST MODE

Figure one shows a preferred embodiment of the magnetic separation device of the present invention. It advantageously accommodates microtubes such as the Micronic ® type tube and most preferably it is made to accommodate 96 such tubes simultaneously in 12 rows by 8 rows or channels. Such an orientation is similar to that of a common usage with respect to Microtiter ® type trays which provide 96 wells. Other manufacturers have made accessory devices for use with such trays, such as for example, the Propet ® pipetting system from Cetus, Emeryville, Calif. By advantageously providing the 96 sample format, the device of the present invention could potentially be used with such automated devices already present in the laboratory.

Figure 1:
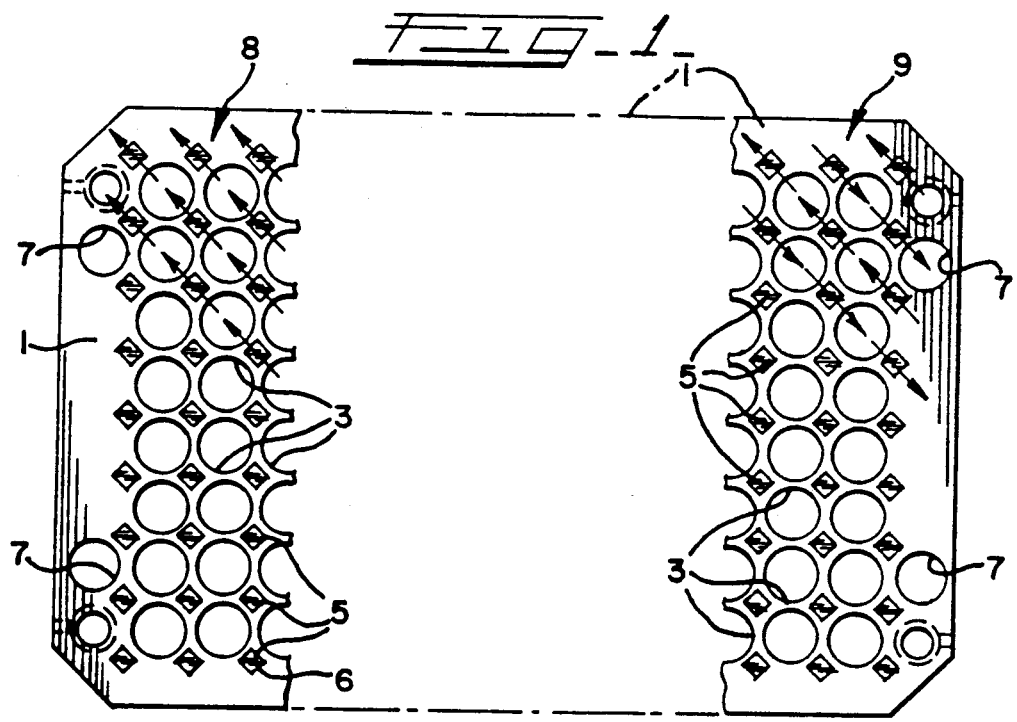
FIG. 1 shows a plan view of the magnetic separation device with 1A showing the installation of a magnet.
Figure 1A:
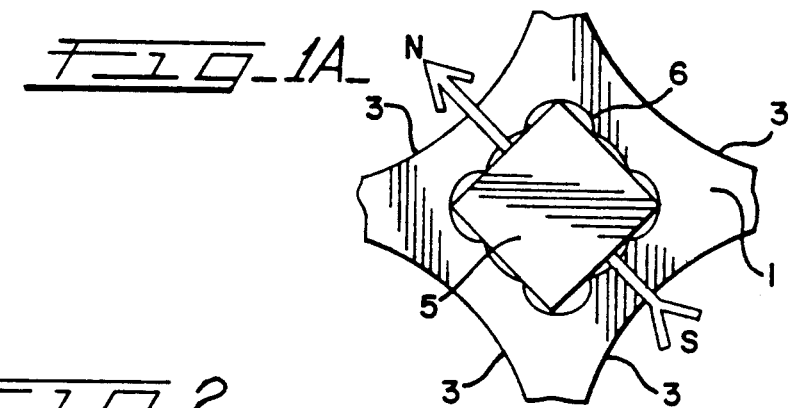
Figure 2:
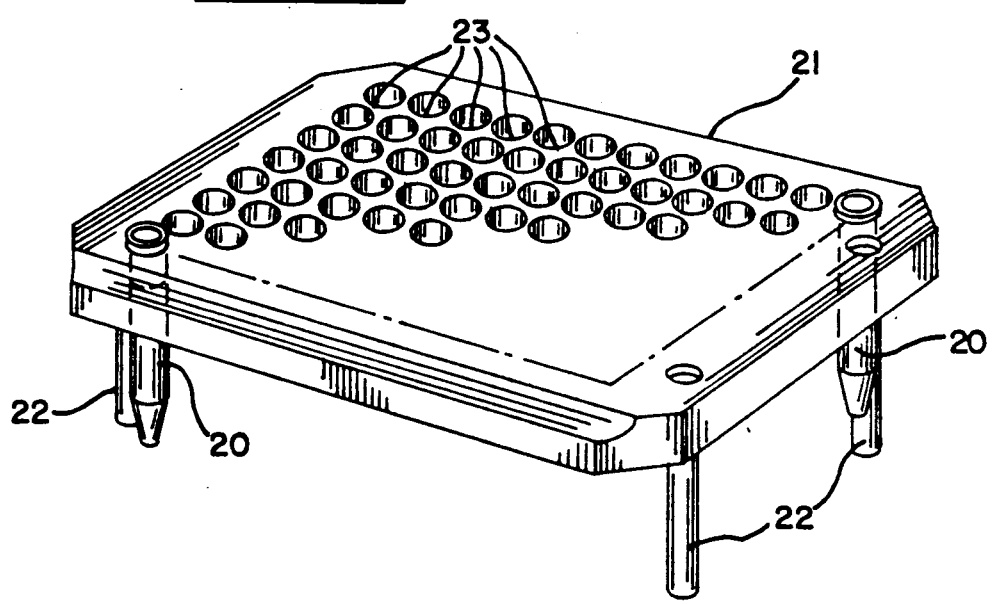
FIG. 2 shows a perspective view of the transfer tray for moving microtubes to and from the magnetic separation device.

FIG. 1 shows the base 1 of the separator device having a plurality of receiving orifice 3 for receiving the microtubes (See FIG. 2, number 20). Preferably, the base will be comprised of a nonferrous or nonmagnetic material and may be advantageously machined out of a metal such as aluminum or molded out of suitable plastic. Most preferably, the materials shall be selected so that they may withstand typical sterilizing procedures such as autoclaving. Surrounding the periphery of orifice 3 are machined orifice 6 (or molded orifice 6) for receiving magnets 5. Having a north-south field orientation which is coplanar with the surface of the base 1 and a cross-section of receiving orifice 3.

If the Neodymium Iron Boron Magnets all aligned in the same "North" direction as shown in FIG. 8, it was discovered that this results in a field strength within the receiving orifice of approximately 500–600 Gauss. If, however, the magnets have an alternate "North" pattern as shown in FIG. 9, e.g., as one proceeds around the clockwise direction of the periphery of each orifice, the magnetic field alternates 180° in direction, it was surprisingly discovered that such an orientation tends to focus the field lines within the receiving orifice and the magnetic field increased to approximately 1400–1600 Gauss. As a result of this surprisingly orientation, a dramatic increase in the separation of magnetic microparticles, such as those available from Advanced Magnetics, Inc., occurs within the solution. As may be apparent, separation results in the localization of four areas or spot attraction sites within the microtube. Less preferred embodiments of the magnetic separation device of the present invention utilize fewer magnets such as 24, or 59, evenly dispersed between receiving orifices 3 in base 1 whereby 1, or 2 respectively spot attraction sites result within each microtube.

Most preferably, the magnets 5 employed are permanent magnets, most preferably possessing a strong magnetic field. The stronger the magnetic field, the more effective the separation and the faster such separation is effective. Most preferred magnetics are rare earth Neodymium Iron Boron magnetics available from IG Technologies, Valparaiso, Indiana. Magnets of 0.13"×0.13"×0.5" were advantageously used as possessing the necessary strength and size requirements so that they could be suitably installed in orifice 6 between receiving orifice 3 which accommodate the microtubes commercially available. Orifice 6, in microtiter plate geometrics can be installed from the top or bottom of the microtiter plate and is based on the manufacturers plate geometry.

While the magnets 5 may be press fit into machine orifice 6, other production techniques may be employed. For example, base 1 could be manufactured by investment casting method whereby magnet orifice 6 possesses a size and shape more closely matching that of magnet 5. Alternately, base 1 may be produced from plastic such as by an injection molding process which also allows for close tolerances in form fitting magnet receiving orifice 6.

FIG. 2 shows a transfer tray for use with the magnetic separation device shown in FIG. 1. Transfer tray 21 possess tube receiving orifice 23 for receiving microtubes 20. Tube transfer tray 21 further comprises tray legs 22 which serve to support to transfer tray 21 a sufficient distance of a surface to allow loading of microtubes 20 and also serve to provide alignment and a vertical height adjustment with tray leg receiving orifice 7 (FIG. 1) upon mateable engagement of the microtubes 20 with receiving orifice 3 (FIG. 1). Proper vertical height alignment is required in the magnetic separator for optimum separation efficiencies.

Receiving tray 21 further assists the operator during the performance of the assay to transfer microtubes 20 to agitation devices for physically urging separated microparticles into solution from their spot attraction sites. The tube transfer tray 21 further assists in transferring the microtubes to an incubator block for providing a temperature controlled environment as required for the particular assay being performed.

FIG. 3 shows a perspective view of the most preferred embodiment wherein receiving base 31, made from a nonferrous metal such as aluminum, is machined to accommodate cylinders 33. preferably again aluminum, dimensioned to accommodate the microtubes. The machined out area of receiving base 31 is also dimensioned to accommodate magnets 35 such that each receiving tube 33 is surrounded by four magnets 35. Most preferably, the magnetic field orientation of magnets 35 are arranged in a alternate pattern as previously discussed. Magnets 35 and tubes 33 are held in place by base cover 32 which may be permanently attached to receiving base 31 by means of screws, adhesives, ribbons and the like. While this most preferred embodiment is shown with nine receiving orifice 37, it will be readily appreciated that this construction embodiment may be scaled up to the 96 receiving orifice (or more as desired) shown in FIG. 1.

FIG. 4 shows a perspective view of receiving based/separator 41 with tube transfer tray 42 mateably engaged therewith with microtubes 43 installed therein. A guided channel pipetter 44 is employed to pipette fluids to and/or from the microtubes through fluid connection tube 47 to the fluid pump mechanism (not shown). The pipetter 44 with individual pipettes for each microtube within a particular row or column engages receiving base/separator 41 by mateable engagement of alignment pegs 45 with alignment holes 46.

Figure 5:
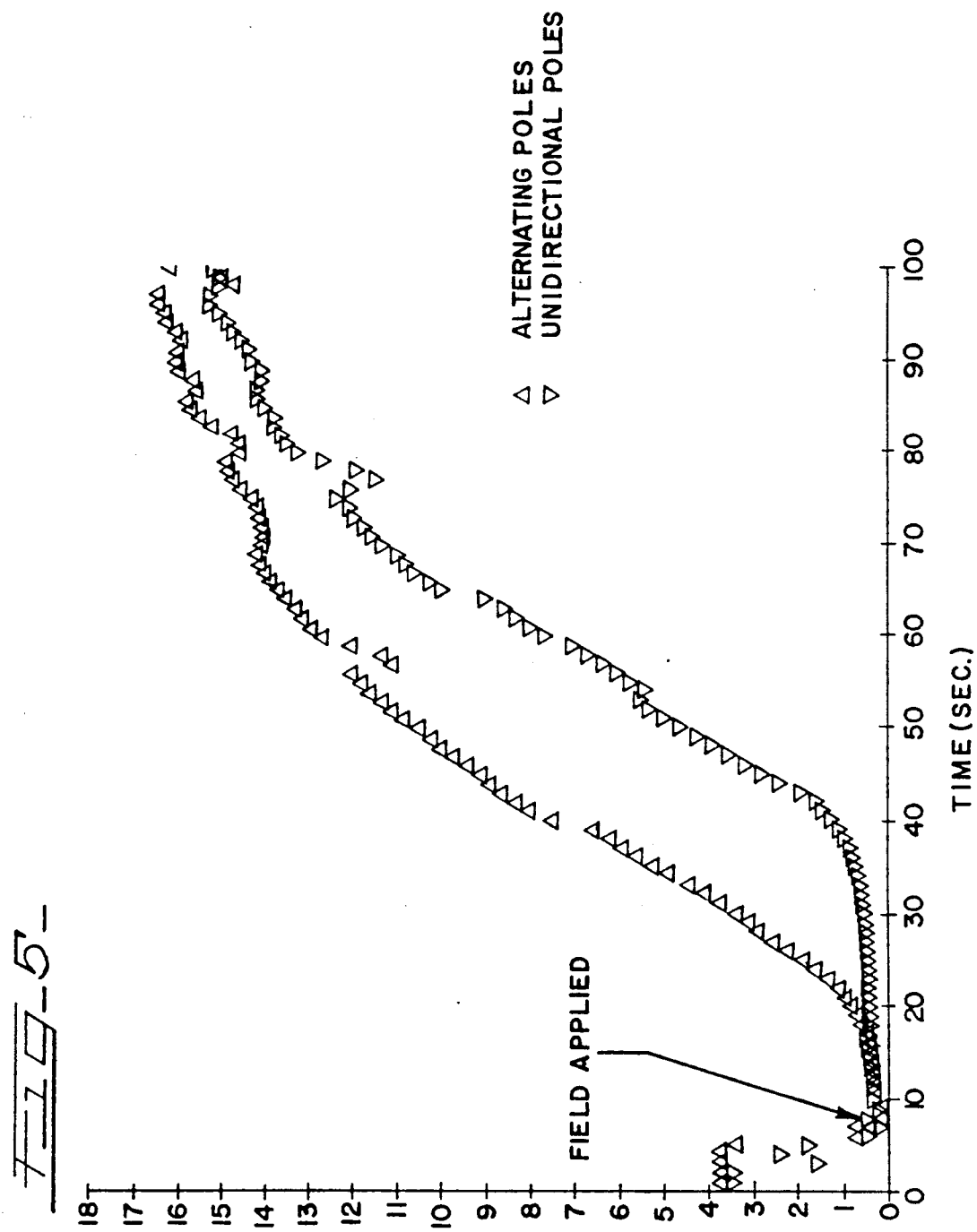
FIG. 5 shows the surprising and unexpected speed advantages gained in separation with alternating magnetic poles over unidirectional magnetic poles.

FIG. 5 shows the results of an experiment directed to measuring the speed of particle movement vs. magnetic orientation as determined by light intensity measured in a spectrophotometer. As will be clearly understood upon study of the figure, it is apparent that a tremendous, surprising and unexpected increase in speed of particle movement is observed in the device of the invention when alternating magnetic poles are utilized. Nonetheless, unit directional poles will generally be adequate for most samples, however, the alternating poles will clearly be preferred with respect to viscous samples such as those containing blood and the like. Accordingly, the preferred embodiment of the present inventions will utilize alternating magnetic poles as shown in area 9 of FIG. 1.

While the present invention has been specifically described with reference to Micronic® type microtubes, it will be readily appreciated that the principles of the invention may be readily applied to microtiter type tray embodiments. Specifically, obvious mechanical alterations to the embodiment shown in the figures will be required in order to adequately receive the microtiter trays and place the magnets in juxtaposition with the wells. Preferably, such placement will involve the utilization of at least four magnets, advantageously spaced evenly about the periphery of each well. Most preferably, the magnetic field orientation will alternate approximately 180° C. with each magnet as one uses the magnets in a clockwise or counterclockwise direction about the periphery of the orifice or other area receiving the well of a microtiter tray. Actual physical embodiments of the base for receiving the microtiter tray may involve exposure of coated magnets whereby the placement of the microtiter tray on top of the base allows the magnets to protrude upwardly between the wells of the microtiter tray. Alternatively, and particularly with respect to that type of microtiter tray which has a solid bottom, the base will simply accommodate the microtiter tray and a cover comprising downwardly protruding magnets will mateably engage with the top of a microtiter tray whereby the magnets protrude downwardly between the microtiter wells. Holes are provided in the top plate for fluid removal. Given the disclosure and particularly the accompanying figures, one skilled in the art will readily determine suitable physical constructions for accommodating the microtiter tray of choice.

Employment of the device will become clear upon review of its use in the following hybridization assay example. Study of this example with the foregoing description and accompanying drawings will make its similar employment in immunoassays obvious to and well within the skill of one of ordinary skill in the art.

EXAMPLE 1
Detection of Listeria Monocytogenes

A DNA probe assay for *Listeria monocytogenes* was performed using 0.5–1.5μ diameter magnetic particles (Advanced Magnetics, Inc.) with oligo dT14 covalently coupled to the surface of the magnetic particles. A base was comprised of 117 magnets glued into a plate which mates with the chosen microtiter plate (Titertek/96 well plates). When the microtiter plate of this assay is mated with the base, each well in the microtiter plate has a magnet at each quadrant, thereby effecting separation of the magnetic particles from the supernatant as described earlier.

An overnight culture of *Listeria* was grown in brain heart infusion broth at 37° C. and 1 ml of this sample culture was added to 1 ml of a processing buffer as defined below and a mixture of 70 ul total was added to each microtiter plate well.

PROCESSING BUFFER
5M GuSCN (guanidine isothiocyanate)
0.30M Tris-HCl, pH 7.5 (Tris-[hydroxymethyl-]aminomethane)
0.10M Na$_2$EDTA (ethylene diaminetetraacetic acid)
20% dextran sulfate (MW 5000) (wt/vol.)

2.0 ul of a 35 mer oligonucleotide of DNA tailed with 160 dA residues (35 ng/ul in 2.5M GuSCN, 10 mM EDTA, pH 7.5) was added to each well and incubated at 37° C. for 15 minutes. 140 ul dT14 derivatized magnetic beads (dA50 binding capacity of 5 ug/ml) in a bead reagent buffer (as defined below) was added to each well:

BEAD REAGENT BUFFER
Tris-HCl 0.1M, pH 7.4
acetylated BSA 0.5% (Bovine Serum Albumin)
10 ug/ml sonicated calf thymus DNA
10 mM EDTA
4% saponin
0.5% sarkosyl
0.5M NaCl
0.1% azide
0.01% silicone antifoaming agent Magnetic beads were separated by mating the microtiter plate with the base containing 117 magnetics and supernatant removed, and 0.1 ml of wash buffer 1 was added to each well at room temperature, and the beads resuspended after unmating the plate from the base containing 117 magnets.

WASH BUFFER 1
1M GuSCN
Tris-HCl 0.1M, pH 7.4
acetylated BSA 0.5%
10 ug/ml calf thymus DNA
EDTA 10 mM
0.1% sodium azide
sarkosyl 0.5%
saponin 1%
antifoam Magnetic beads were reseparated by mating the microtiter plate with the base containing 117 magnet, supernatant removed, 0.1 ml of wash buffer 1 added at room temperature, and the beads resuspended after unmating the plate from the base containing 117 magnets.

Magnetic beads were reseparated by mating the microtiter plate with the base containing 117 magnet, supernatant removed, 0.1 ml of wash buffer 1 added at room temperature, and the beads resuspended after unmating the plate from the base containing 117 magnets.

65 ul of chemical eluant (defined below) was added to each well, the constructs mixed and incubated for two minutes at 37° C.

CHEMICAL ELUANT
2.5M GuSCN
Tris-HCl 0.1M, pH 7.4
10 ug/ml sonicated calf thymus DNA
acetylated BSA 0.5%
EDTA 10 mM
1.0% saponin
0.5% sarkosyl Magnetic beads were separated by mating the microtiter-plate with the base containing 117 magnets and the eluate from each well transferred to a fresh well containing ul of a 14 ng/ml concentration of riboprobe cloned from the 3'-end of *E. coli*. The mixture was incubated at 37° C. for four minutes. 140 ul of beads in reagent (dA50 binding capacity of >5 ug/ml), was added to each well and incubated for two minutes at 37° C., the beads magnetically separated by mating the microtiter plate with the base containing 117 magnets at 37° C.

The supernatant was removed and 0.1 ml of wash buffer 2 (defined below) added to each well and the beads resuspended at 37° C. after unmating the base from the microtiter plate.

WASH BUFFER
Tris 0.1M, pH 7.4
10 ug/ml *E. coli* DNA or t-RNA
EDTA 10 mM
acetylated BSA 0.5%
0.5M NaCl
0.5% sarkosyl Magnetic beads were separated by mating the microtiter plate with the base containing 117 magnets, supernatant removed, 0.1 ml of wash buffer 2 added at 37° C., and the beads resuspended after unmating the plate from the base containing 117 magnets.

Separate magnetic beads by mating the microtiter plate with the base containing 117 magnets, supernatant removed, 0.1 ml of wash buffer 2 added at 37° C., and the beads resuspended after unmating the plate from the base containing 117 magnets.

Magnetic beads were separated by mating the microtiter plate with the base containing 117 magnets, supernatant removed, 0.1 ml of wash buffer 2 added at 37° C., and the beads resuspended after unmating the plate from the base containing 117 magnets.

Separate magnetic beads by mating the microtiter plate with the base containing 117 magnets, supernatant removed, 0.1 ml of wash buffer 2 added at 37° C., and the beads resuspended after unmating the plate from the base containing 117 magnets.

Magnetic beads were separated by mating the microtiter plate with the base containing 117 magnets, supernatant removed, 0.1 ml of wash buffer 2 added at 37° C., and the beads after unmating the plate from the base containing 117 magnets.

Separate magnetic beads by mating the microtiter plate with the base containing 117 magnets, supernatant removed, 0.1 ml of wash buffer 2 added at 37° C., and the beads resuspended after unmating the plate from the base containing 117 magnets.

Magnetic beads were separated by mating the microtiter plate with the base containing 117 magnets, supernatant removed, 0.1 ml of wash buffer 2 added at 37° C., and the beads resuspended after unmating the plate from the base containing 117 magnets.

100 ul wash buffer 2 was added for each well and incubated at 68° C. for two minutes.

Beads were magnetically separated by mating the microtiter plate with the base containing 117 magnets and supernatant removed and transferred to scintillation fluid and then the amount of $P^{32}$ in each vial was determined by use of a Beckman 1800 scintillation counter. The presence of Listeria was confirmed by $P^{32}$ counts that were more than an order of magnitude greater than when Listeria was absent in control wells.

What is claimed is:

1. A magnetic separation apparatus for use in assays employing solid phases comprising magnetic particles, said apparatus comprising:
   (a) base means having a plurality of orifices for receiving nonferrous containers adapted to contain said magnetic particles; and
   (b) a plurality of magnet means mounted on said base and spaced about the periphery of each receiving orifice wherein each of said magnet means possess a north-south magnetic field orientation in a direction which is coplanar with a cross-sectional plane through said receiving orifices and wherein each of said north-south magnetic fields of said magnet means are oriented in a common direction and wherein said magnet means are mounted in a fixed relation with respect to themselves and to said base whereby each nonferrous container, when placed in receiving relationship with each of said orifices, has four magnet means about its periphery.

2. The apparatus of claim 1 wherein said magnet means is a rare earth cobalt magnet.

3. The apparatus of claim 2 wherein said magnet means is a 33H Neodymium Iron Boron magnet.

4. The apparatus of claim 1 further comprising tube transfer means adapted to receive nonferrous microtube containers and to mateably engage said base means whereby each nonferrous microtube container is received by a receiving orifice and is surrounded by a plurality of magnets.

5. A process for detecting a ligand in a fluid sample by immunoassay or hybridization with a ligand specific binding substance which utilizes a ferrous solid phase microparticle wherein the improvement comprises employing the magnetic separation apparatus of claim 1 for effecting separation of solid phase bound ligands or ligand specific binding substances from unbound ligands or ligand specific binding substances present in said fluid sample.

6. A magnetic separation apparatus for use in assays employing solid phases comprising magnetic particles, said apparatus comprising:
   (a) a base means having a plurality of orifices for receiving nonferrous containers adapted to contain said magnetic particles; and
   (b) a plurality of magnet means mounted on said base spaced about the periphery of each receiving orifice and wherein said magnet means are mounted in a fixed relation with respect to themselves and to said base and wherein each of said magnet means possess a north-south magnetic field orientation in a direction which is coplanar with a cross-sectional plane through said receiving orifices and wherein the north-south magnetic field direction orientation, moving in a common direction about the periphery of each of said receiving orifices, alternates approximately 180° from the north-south field direction orientation of the preceding magnet whereby each nonferrous container, when placed in receiving relationship with each of said orifices, has four magnet means about its periphery.

7. The apparatus of claim 6 wherein said magnet means is a rare earth cobalt magnet.

8. The apparatus of claim 7 wherein said magnet means is a 33H Neodymium Iron Boron magnet.

9. The apparatus of claim 8 wherein said base means has 96 receiving orifices, said apparatus comprises 117 33H Neodymium Iron Boron magnets and said base means is made of a material selected from the group consisting of aluminum and plastic.

10. The apparatus of claim 9 wherein said magnets have a dimension of approximately 0.13×0.13×0.5 inches.

11. The apparatus of claim 6 further comprising tube transfer means adapted to receive nonferrous microtube containers and to mateably engage said base means whereby each nonferrous microtube container is received by a receiving orifice and is surrounded by a plurality of magnets.

12. A process for detecting a ligand in a fluid sample by immunoassay or hybridization with a ligand specific binding substance which utilizes a ferrous solid phase microparticle wherein the improvement comprises employing the magnetic separation apparatus of claim 6 for effecting separation of solid phase bound ligands or ligand specific binding substances from unbound ligands or ligand specific binding substances present in said fluid sample.

13. The apparatus of claim 12 wherein said magnet means is a rare earth cobolt magnet.

14. The apparatus of claim 13 wherein said magnet means is a rare earth cobolt magnet.

15. A magnetic separation apparatus for use in assays employing solid phases comprising magnetic particles, said apparatus comprising:
   (a) base means adapted to receive microwell tray means of nonferrous composition adapted to contain said magnetic particles; and
   (b) a plurality of magnet means mounted on said base in spatial alignment with said microwell tray means whereby each well in said microwell tray means has adjacent thereto at least one magnet means possessing a north-south magnetic field orientation in a direction which is coplanar with a cross-sectional plane through said well and wherein each of said north-south magnetic fields of said magnet means are oriented in a common direction and wherein said magnet means are mounted in a fixed relation with respect to themselves and to said base whereby each nonferrous container, when placed in receiving relationship with each of said wells, has four magnet means about its periphery.

16. A magnetic separation apparatus for use in assays employing solid phases comprising magnetic particles, said apparatus comprising:
    (a) base means adapted to receive microwell tray means of nonferrous composition adapted to contain said magnetic particles and having a plurality of wells; and
    (b) a plurality of magnet means mounted on said base in spatial alignment with said microwell tray means wherein said magnet means are mounted in a fixed relation with respect to themselves and to said base and wherein each of said magnet means possess a north-south magnetic field orientation in a direction which is coplanar with a cross-sectional plane through said microwell tray means and wherein the north-south magnetic field direction orientation, moving in a common direction about the periphery of each well in said microwell tray means, alternates approximately 180° from the forth-south field direction orientation of the preceding magnet thereby each well of said microwell tray means, when placed in receiving relationship with said base means, has four magnet means about its periphery.

17. A magnetic separation apparatus for use in assays employing solid phases comprising magnetic particles, said apparatus comprising:
    a. base means for receiving a nonferrous tray containing a plurality of microwells adapted to contain said magnetic particles;
    b. base means comprising a plurality of magnet means mounted on said base spaced on said base whereby engagement of said base and said tray results in the juxtapose placement of a plurality of magnet means about the periphery of each well wherein each of said wells is surrounded about the perhiphery by four magnet means wherein the north-south magnetic field direction orientation, moving in a common direction about the periphery of each of said wells, alternates approximately 180° from the north-south field direction orientation of the preceding magnet.

* * * * *